US006500797B1

(12) United States Patent
Ortiz et al.

(10) Patent No.: US 6,500,797 B1
(45) Date of Patent: Dec. 31, 2002

(54) PROCESS FOR PREPARING β-KETOESTER FRAGRANCE PRO-ACCORDS FROM 1,3-DIOXAN-4,6-DIONES

(75) Inventors: Rafael Ortiz, Milford, OH (US); Lee Arnold Schectman, Fairfield, OH (US); Mark Robert Sivik, Fairfield, OH (US); John August Wos, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/509,357
(22) PCT Filed: Aug. 28, 1998
(86) PCT No.: PCT/IB98/01340

§ 371 (c)(1),
(2), (4) Date: Mar. 23, 2000

(87) PCT Pub. No.: WO99/16740

PCT Pub. Date: Apr. 8, 1999

Related U.S. Application Data

(60) Provisional application No. 60/060,359, filed on Sep. 29, 1997.

(51) Int. Cl.$^7$ .................................................. A61K 7/46
(52) U.S. Cl. .................................. 512/27; 512/2; 512/3; 512/25; 512/26; 554/115; 560/126; 560/51; 560/174
(58) Field of Search .................. 560/126, 51, 174; 554/115; 512/2, 3, 25, 26, 27

(56) References Cited

U.S. PATENT DOCUMENTS 5,965,767 A * 10/1999 Sivik et al. .................. 560/126

FOREIGN PATENT DOCUMENTS

WO    WO 98/07405    *    2/1998

OTHER PUBLICATIONS

Houghton et al. "A Modified Preparation of B–Keto Esters", Synthesis, No. 6, 1982 451–452.*
Oikawa et al. "Meldrum's Acid in Organic Synthesis", J. Organic Chemistry, vol. 43, No. 10, 1978.*

* cited by examiner

*Primary Examiner*—Jan Ludlow
*Assistant Examiner*—Monique T. Cole
(74) *Attorney, Agent, or Firm*—James F. McBride; Kim W. Zerby; Steven W. Miller

(57) ABSTRACT

The present invention relates to methods for preparing β-ketoester fragrance pro-accords from activated acyl units, 1,3-dioxan-4,6-diones and fragrance raw material alcohols. The first step involves contacting an activated acyl unit, preferably an acid chloride, with a 1,3-dioxan-4,6-dione, an example of which is Meldrum's acid, to form a 2-acyl 1,3-dioxan-4,6-dione which is then reacted with a fragrance raw material alcohol to form the final β-ketoester fragrance pro-accord. The resulting β-ketoester fragrance pro-accords are suitable for use in laundry detergent, personal care, and other formulations wherein aesthetic fragrance materials are employed.

21 Claims, No Drawings

PROCESS FOR PREPARING β-KETOESTER FRAGRANCE PRO-ACCORDS FROM 1,3-DIOXAN-4,6-DIONES

This application claims the benefit of Provisional application Ser. No. 60/060,359, filed Sep. 29, 1997.

FIELD OF THE INVENTION

The present invention relates to methods for preparing β-ketoester fragrance pro-accords, said pro-accords useful for providing sustained fragrance to items which deliver perfume for aesthetic reasons inter alia laundry detergent compositions, fabric softeners, personal care and personal hygiene items, shampoos, body lotions, and fabric re-fresheners. The process of the present invention relates to the use of 1,3-dioxane-4,6-diones as a synthon for the facile formation of β-ketoesters, especially β-ketoesters which comprise a tertiary alcohol subunit.

BACKGROUND OF THE INVENTION

Esters which release perfume alcohols are currently of interest for their different odor profiles in products, as well as their odor profiles during and after use. Particularly desirable are such esters which have a prolonged release characteristic from use in a home laundering process. Deposition onto a substrate, for example, onto fabric during the wash process followed by delayed release of the perfume after drying, is especially desirable. The challenge for using such esters include not only the right combination of storage stability and odor release profile, but also the challenge of making such esters in a cost effective manner.

β-Ketoesters are a particularly desirable class of materials, but such materials can present a particular challenge for a cost effective production. The di-functionality (ketone and carboxylic ester functionality in the same compound) of these compounds limits the types of reactions and conditions under which these compounds can be made. Add on the industrial scale and cost constraints that the use of specialty reactants add to the possible synthesis methods, and the large scale of production of such β-ketoester compounds for use in high volume consumer products becomes problematic.

Accordingly there remains a need in the art for a method for a simple, high yield, cost-effective means for preparing β-ketoester fragrance pro-accords. In addition there is a need for convenient methods which produce β-ketoesters capable of releasing tertiary alcohols inter alia dihydromyrcenol and linalool.

BACKGROUND ART

The following relate to the preparation of β-ketoesters from 1,3-dioxane-4,6-diones. Oikawa et al., *J. Org. Chem.*, Vol 43, No 10, 1978, pg. 2087; Capozzi et al., *J. Org. Chem.*, Vol 58, No 27, 1993, pg. 7932; Organic Synthesis Collective Volumes, pg 359, Oikawa et al., submitters; and Houghton et al., "A Modified Preparation of β-Keto Esters", *Synthesis*, pg 451, (1982).

SUMMARY OF THE INVENTION

It has now been surprisingly discovered that molecules which releasably comprise fragrance raw material alcohols, namely β-ketoester fragrance pro-accords, can be suitably prepared from activated acyl adducts, for example, acid chlorides, and 1,3-dioxan-4,6-diones followed by reacting the product with a fragrance raw material alcohol. It is especially desirable that the fragrance raw material alcohols which become a subunit of the β-ketoester fragrance pro-accord are tertiary alcohols, for example, linalool and dihydromycenol.

The first aspect of the present invention relates to a process for preparing β-ketoester fragrance pro-accords comprising the steps of:

a) reacting in the presence of a base a 1,3-dioxane-4,6-dione having the formula:

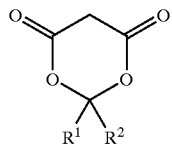

wherein $R^1$ and $R^2$ are each independently $C_1$–$C_{10}$ alkyl, $C_2$–$C_{10}$ alkenyl, $C_7$–$C_{22}$ alkylenearyl, $C_6$–$C_{10}$ aryl, and mixtures thereof; with an activated acyl group having the formula:

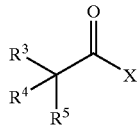

wherein $R^3$, $R^4$, and $R^5$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_1$–$C_{30}$ substituted or unsubstituted linear alkoxy, $C_3$–$C_{30}$ substituted or unsubstituted branched alkoxy, $C_3$–$C_{30}$ substituted or unsubstituted cyclic alkoxy, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl; or $R^3$, $R^4$, and $R^5$ can be taken together to form $C_6$–$C_{30}$ substituted or unsubstituted aryl; and mixtures thereof; X is an acyl activating unit; to form an acyl 1,3-dioxane-4,6-dione, the enol tautomer of which having the formula:

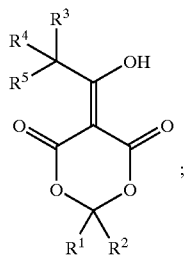

b) optionally, isolating said acyl 1,3-dioxane-4,6-dione; and c) reacting said acyl 1,3-dioxane-4,6-dione from step (a) or (b) with a fragrance raw material alcohol having the formula:

ROH to form a β-ketoester fragrance pro-accord having the formula:

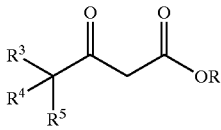

wherein $R^3$, $R^4$, and $R^5$ are the same as defined herein above.

The present invention more specifically relates to the preparation of β-ketoester fragrance pro-accords which comprise a secondary or tertiary alcohol subunit, more preferably a tertiary alcohol subunit. These and other objects, features and advantages will become apparent to those of ordinary skill in the art from a reading of the following detailed description and the appended claims.

All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

The present invention relates to a process for preparing β-ketoester fragrance pro-accords from 1,3-dioxan-4,6-diones, preferably from 2,2-dimethyl-1,3-dioxan-4,6-dione. Variations of the present process include isolation and purification of the intermediate acyl 1,3-dioxane-4,6-dione formed in Step (a) prior to subsequent reaction with a fragrance raw material alcohol. However, the formulator, depending upon several variables inter alia the structure of the final β-ketoester, the amount of material to be produced, the type of process (i.e. batch reactions vs. continuous process) may produce the final product without isolation of the acyl 1,3-dioxan-4,6-dione intermediate.

For the purposes of the present invention the term "substituted" as it applies to linear alkyl, branched alkyl, cyclic alkyl, linear alkenyl, branched alkenyl, cyclic alkenyl, branched alkoxy, cyclic alkoxy, alkynyl, and branched alkynyl units are defined as "carbon chains which comprise substitutents other than branching of the carbon atom chain", for example, other than the branching of alkyl units (e.g. isopropyl, isobutyl). Non-limiting examples of "substituents" include hydroxy, $C_1$–$C_{12}$ alkoxy, preferably methoxy; $C_3$–$C_{12}$ branched alkoxy, preferably isopropoxy; $C_3$–$C_{12}$ cyclic alkoxy; nitrilo; halogen, preferably chloro and bromo, more preferably chloro; nitro; morpholino; cyano; carboxyl, non-limiting examples of which are —CHO; —$CO_2^-M^+$; —$CO_2R^9$; —$CONH_2$; —$CONHR^9$; —$CONR^9_2$; wherein $R^9$ is $C_1$–$C_{12}$ linear or branched alkyl); —$SO_3^-M^+$; —$OSO_3^-M^+$; —$N(R^{10})_2$; and —$N^+(R^{10})_3X^-$ wherein each $R^{10}$ is independently hydrogen or $C_1$–$C_4$ alkyl; and mixtures thereof; wherein M is hydrogen or a water soluble cation; and X is chlorine, bromine, iodine, or other water soluble anion.

For the purposes of the present invention substituted or unsubstituted alkyleneoxy units are defined as moieties having the formula:

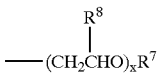

wherein $R^7$ is hydrogen; $R^8$ is hydrogen, methyl, ethyl, and mixtures thereof; the index x is from 1 to about 10.

For the purposes of the present invention substituted or unsubstituted alkyleneoxyalkyl are defined as moieties having the formula:

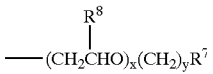

wherein $R^7$ is hydrogen, $C_1$–$C_{18}$ alkyl, $C_1$–$C_4$ alkoxy, and mixtures thereof; $R^8$ is hydrogen, methyl, ethyl, and mixtures thereof; the index x is from 1 to about 10 and the index y is from 2 to about 18.

For the purposes of the present invention substituted or unsubstituted aryl units are defined as phenyl moieties having the formula:

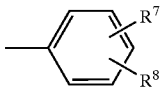

or α and β-naphthyl moieties having the formula:

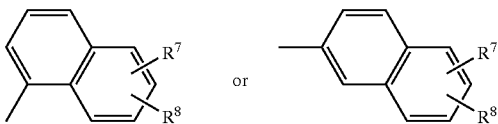

wherein $R^7$ and $R^8$ can be substituted on either ring, alone or in combination, and $R^7$ and $R^8$ are each independently hydrogen, hydroxy, $C_1$–$C_6$ alkyl, $C_2$–$C_6$ alkenyl, $C_1$–$C_4$ alkoxy, $C_3$–$C_6$ branched alkoxy, nitrilo, halogen, nitro, morpholino, cyano, carboxyl (—CHO; —$CO_2^-M^+$; —$CO_2R^9$; —$CONH_2$; —$CONHR^9$; —$CONR^9_2$; wherein $R^9$ is $C_1$–$C_{12}$ linear or branched alkyl), —$SO_3^-M^+$, —$N(R^{10})_2$, and —$N^+(R^{10})_3X^-$ wherein each $R^{10}$ is independently hydrogen, $C_1$–$C_4$ alkyl or mixtures thereof; and mixtures thereof, $R^7$ and $R^8$ are preferably hydrogen, $C_1$–$C_6$ alkyl, —$CO_2^-M^+$, —$SO_3^-M^+$, —$OSO_3^-M^+$, and mixtures thereof; more preferably $R^7$ or $R^8$ is hydrogen and the other moiety is $C_1$–$C_6$; wherein M is hydrogen or a water soluble cation and X is chlorine, bromine, iodine, or other water soluble anion. Examples of other water soluble anions include organic species such as fumarate, succinate, tartrate, oxalate and the like, inorganic species include sulfate, hydrogen sulfate, phosphate and the like.

For the purposes of the present invention substituted or unsubstituted alkylenearyl units are defined as moieties having the formula:

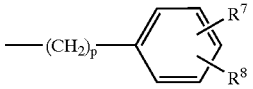

wherein $R^7$ and $R^8$ are each independently hydrogen, hydroxy, $C_1$–$C_4$ alkoxy, nitrilo, halogen, nitro, carboxyl (—CHO; —$CO_2^-M^+$; —$CO_2R^9$; —$CONH_2$; —$CONHR^9$; —$CONR^9_2$; wherein $R^9$ is $C_1$–$C_{12}$ linear or branched alkyl), amino, alkylamino, and mixtures thereof, p is from 1 to about 14; M is hydrogen or a water soluble cation.

For the purposes of the present invention substituted or unsubstituted alkyleneoxyaryl units are defined as moieties having the formula:

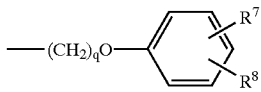

wherein $R^7$ and $R^8$ are each independently hydrogen, hydroxy, $C_1$–$C_4$ alkoxy, nitrilo, halogen, nitro, carboxyl (—CHO; —CO$_2$$^-$M$^+$; —CO$_2$R$^9$; —CONH$_2$; —CONHR$^9$; —CONR$^9$$_2$; wherein $R^9$ is $C_1$–$C_{12}$ linear or branched alkyl), amino, alkylamino, and mixtures thereof, q is from 1 to about 14; M is hydrogen or a water soluble cation.

The following summarizes the process of the present invention.

Step (a) Formation of a 2-acyl-1,3-dioxan-4,6-dione

The first step of the process of the present invention relates to reacting an activated acyl moiety of the general formula:

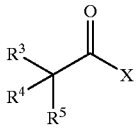

with a 1,3-dioxan-4,6-dione having the formula:

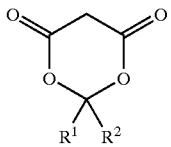

to form a 2-acyl-1,3-dioxan-4,6-dione having, in its enol tautomer form, the formula:

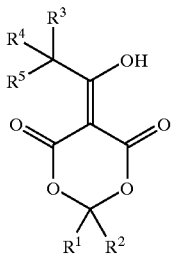

wherein $R^1$ and $R^2$ are each independently $C_1$–$C_{10}$ alkyl, $C_2$–$C_{10}$ alkenyl, $C_7$–$C_{22}$ alkylenearyl, $C_6$–$C_{10}$ aryl, and mixtures thereof, preferably methyl; wherein $R^3$, $R^4$, and $R^5$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_1$—$C_{30}$ substituted or unsubstituted linear alkoxy, $C_3$–$C_{30}$ substituted or unsubstituted branched alkoxy, $C_3$–$C_{30}$ substituted or unsubstituted cyclic alkoxy, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl; or $R^3$, $R^4$, and $R^5$ can be taken together to form $C_6$–$C_{30}$ substituted or unsubstituted aryl; and mixtures thereof; preferably two of $R^3$, $R^4$, and $R^5$ are hydrogen and the remaining group is $C_1$–$C_{10}$ linear or branched alkyl, $C_2$–$C_{10}$ linear or branched alkenyl, preferably methyl and octyl, also preferably $R^3$, $R^4$, and $R^5$ are taken together to form a substituted or unsubstituted phenyl, substituted or unsubstituted naphthyl, more preferably naphthyl.

X is an acyl activating unit. Non limiting examples of acyl activating units are acyloxy units having the formula —OC(O)R' which when taken together with the acyl moiety form a symmetrical or non-symmetrical anhydride, wherein R' is the same or different than the moiety which is formed by $R^3$, $R^4$, and $R^5$. However, in cases where anhydride-like conditions are desired and formation of the acyl unit anhydride is either impractical or unobtainable, then the acyl carboxylic acid may be condensed with the 1,3-dioxan-4,6-dione in the presence of a condensing agent such as ethyl phosphonocyanidate. Other non-limiting examples of activated acyl units are acyl acid halides wherein X is chlorine, bromine, iodine, and mixtures thereof, activated esters, for example, 4-nitrophenyl esters of the acyl unit defined by $R^3$, $R^4$, and $R^5$.

The reaction of Step (a) of the present process is conducted in the presence of a base suitable to de-protonate the 2-position carbon of the selected 1,3-dioxan-4,6-dione. The acidity of the protons on the 2-carbon of the 1,3-dioxan-4,6-dione, and therefore the strength of the base necessary for reaction of Step (a), is governed by a number of factors, notably the structure of the dione itself. Bases suitable for use are selected from the group consisting of alkylamines, aromatic amines, polymeric amines, organo lithium compounds, alkali metal hydroxides, alkaline earth metal hydroxides, alkali metal carbonates, alkaline earth metal carbonate, alkali metal hydrides, alkaline earth metal hydrides, and mixtures thereof.

Non-limiting examples of bases suitable for use in the present invention are aromatic amines, for example, pyridine, picoline, lutidine, collidine; mono-, di-, and tri-alkylamines, for example, methyl amine, trimethylamine, triethanolamine; alkali metal and alkaline earth metal hydrides, for example, lithium hydride, sodium hydride; alkali metal alkoxides, for example, sodium ethoxide, sodium methoxide; alkali metal and alkaline earth metal carbonates and bicarbonates, for example sodium carbonate, potassium carbonate; organo metallic compounds, for example, butyl lithium, t-butyl lithium; alkali metal and alkaline earth metal hydroxides, for example, sodium hydroxide, potassium hydroxide. Preferred bases are pyridine and sodium hydride.

Depending upon the reaction conditions desired by the formulator, Step (a) can be conducted in the presence of a suitable solvent. Non-limiting examples of suitable solvents include dichloromethane, 1,2-dichloroethane, 1,2,3-trichloroethane, pentane, hexane, tetrahydrofuran, diethyl ether, benzene, toluene, xylene, 1,4-dioxane, acetonitrile, and mixtures thereof. In addition, the formulator may wish to adjust the reaction conditions to stabilize the formation of charged reaction species in which the use of solvents such as N,N-dimethylformamide (DMF), dimethylsulfoxide (DMSO), hexamethyl phosphoramide (HMPA), and the like may be used alone or in combination with other suitable solvents. However, the formulator may generate the 1,3-dioxan-4,6-dione anion in water followed by isolation of the 1,3-dioxan-4,6-dione salt typically followed by thorough drying.

The reaction of Step (a) may be successfully conducted, depending upon the reactivity of the reagents, the scope of the reaction, and other mitigating parameters, at a temperature of from about −70° C., preferably from about −33° C., more preferably from about 0° C., most preferably from about 22° C.(approximately room temperature), to about 100° C., preferably to about 80° C., more preferably to about 60° C., most preferably to about 40° C. The reaction of Step (a) may be conducted at more than one temperature, for example, during the addition of reagents the temperature of the reaction may be held at a first temperature, for example 0° C., and allowed to warm to a second temperature after the addition is complete. Alternatively, the reaction may be warmed to generate the 1,3-dioxane-4,6-dione anion, then cooled during the addition of the activated acyl adduct.

The reaction of Step (a) may be conducted in any order which insures formation of the desired acyl 1,3-dioxan-4,6-dione intermediate. For example, in a first reaction vessel a suitable 1,3-dioxan-4,6-dione is reacted with sufficient base to form a 1,3-dioxan-4,6-dione anion. This can be accomplished by first charging a dry reaction vessel with an equivalent of a base such as sodium hydride in a suitable solvent such as tetrahydrofuran (THF). In a second reaction vessel a suitable 1,3-dioxan-4,6-dione is dissolved in a suitable solvent, for example, 2,2-dimethyl-1,3-dioxan-4,6-dione in a sufficient amount of dry THF Next the contents of the second reaction vessel is added to the contents of the first reaction vessel while cooling the admixture. Once the 1,3-dioxan-4,6-dione anion is sufficiently formed, in a third reaction vessel, an activated acyl unit is dissolve in a sufficient amount of solvent, for example, 2-naphthoyl chloride, is dissolved in THF, and this solution is subsequently added to the solution of 1,3-dioxan-4,6-dione anion.

However, in other embodiments of the present invention, it may be necessary to warm the admixture of base, suitable 1,3-dioxan-4,6-dione, and solvent in a reaction vessel in order to fully generate the 1,3-dioxan-4,6-dione anion prior to addition of the activated acyl unit.

Also included in Step (a) of the present invention is neutralization of any remaining base prior to proceeding to Steps (b) or (c). In a preferred embodiment of the present process, Step (a) is conducted under an inert atmosphere. Step (b) Optionally Isolating the 2-acyl-1,3-dioxan-4,6-dione formed in Step (a).

The formulator may choose to optionally isolate the 2-acyl-1,3-dioxan-4,6-dione form in Step (a) of the process of the present invention. Isolation may include, distillation, crystallization, chromatography and the like. However, it is not necessary that the intermediate 2-acyl-1,3-dioxan-4,6-dione be isolated prior to Step (c).

Step (c): Reacting the acyl 1,3-dioxane-4,6-dione formed in Step (a) or alternatively isolated in Step (b) with a fragrance raw material alcohol The 2-acyl-1,3-dioxan-4,6-dione form in Step (a) is then reacted with a fragrance raw material alcohol to form a β-ketoester having the formula:

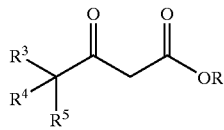

wherein —OR represents a unit derived form a fragrance raw material alcohol an dR³, R⁴, and R⁵ are the same as define herein above.

For the purposes of the present invention "fragrance raw material alcohols" are herein defined as alcohols having a molecular weight and which are useful in imparting an odor, fragrance, essence, or scent either alone or in combination with other "fragrance raw material alcohols".

Non-limiting examples of preferred fragrance raw material alcohols include 2,4-dimethyl-3-cyclohexene-1-methanol (Floralol), 2,4-dimethyl cyclohexane methanol (Dihydro floralol), 5,6-dimethyl-1-methylethenylbicyclo[2.2.1]hept-5-ene-2-methanol (Arbozol), α,α,-4-trimethyl-3-cyclohexen-1-methanol (α-terpineol), 2,4,6-trimethyl-3-cyclohexene-1-methanol (Isocyclo geraniol), 4-(1-methylethyl)cyclohexane methanol (Mayol), α-3,3-trimethyl-2-norborane methanol, 1,1-dimethyl-1-(4-methylcyclohex-3-enyl)methanol, 2-phenylethanol, 2-cyclohexyl ethanol, 2-(o-methylphenyl)-ethanol, 2-(m-methylphenyl)ethanol, 2-(p-methylphenyl)ethanol, 6,6-dimethylbicyclo-[3.1.1]hept-2-ene-2-ethanol (nopol), 2-(4-methylphenoxy)-ethanol, 3,3-dimethyl-Δ²-β-norbomane ethanol (patchomint), 2-methyl-2-cyclohexylethanol, 1-(4-isopropylcyclohexyl)-ethanol, 1-phenylethanol, 1,1-dimethyl-2-phenylethanol, 1,1-dimethyl-2-(4-methyl-phenyl)ethanol, 1-phenylpropanol, 3-phenylpropanol, 2-phenylpropanol (Hydrotropic Alcohol), 2-(cyclododecyl) propan-1-ol (Hydroxy-ambran), 2,2-dimethyl-3-(3-methylphenyl)-propan-1-ol (Majantol), 2-methyl-3-phenylpropanol, 3-phenyl-2-propen-1-ol (cinnamyl alcohol), 2-methyl-3-phenyl-2-propen-1-ol (methylcinnamyl alcohol), α-n-pentyl-3-phenyl-2-propen-1-ol (α-amyl-cinnamyl alcohol), ethyl-3-hydroxy-3-phenyl propionate, 2-(4-methylphenyl)-2-propanol, 3-(4-methylcyclohex-3-ene)butanol, 2-methyl-4-(2,2,3-trimethyl-3-cyclopenten-1-yl)butanol, 2-ethyl-4-(2,2,3-trimethyl-cyclopent-3-enyl)-2-buten-1-ol, 3-methyl-2-buten-1-ol (prenol), 2-methyl-4-(2,2,3-trimethyl-3-cyclopenten-1-yl)-2-buten-1-ol, ethyl 3-hydroxybutyrate, 4-phenyl-3-buten-2-ol, 2-methyl-4-phenylbutan-2-ol, 4-(4-hydroxyphenyl)butan-2-one, 4-(4-hydroxy-3-methoxyphenyl)-butan-2-one, 3-methyl-pentanol, 3-methyl-3-penten-1-ol, 1-(2-propenyl)cyclopentan-1-ol (plinol), 2-methyl-4-phenylpentanol (Pamplefleur), 3-methyl-5-phenylpentanol (Phenoxanol), 2-methyl-5-phenylpentanol, 2-methyl-5-(2,3-dimethyltricyclo[2.2.1.0$^{(2,6)}$]hept-3-yl)-2-penten-1-ol (santalol), 4-methyl-1-phenyl-2-pentanol, 5-(2,2,3-trimethyl-3-cyclopentenyl)-3-methylpentan-2-ol (sandalore), (1-methyl-bicyclo[2.1.1]hepten-2-yl)-2-methylpent-1-en-3-ol, 3-methyl-1-phenylpentan-3-ol, 1,2-dimethyl-3-(1-methylethenyl)cyclopentan-1-ol, 2-isopropyl-5-methyl-2-hexenol, cis-3-hexen-1-ol, trans-2-hexen-1-ol, 2-isoproenyl-4-methyl-4-hexen-1-ol (Lavandulol), 2-ethyl-2-prenyl-3-hexenol, 1-hydroxymethyl-4-isopropenyl-1-cyclohexene (Dihydrocuminyl alcohol), 1-methyl-4-isopropenylcyclohex-6-en-2-ol (carvenol), 6-methyl-3-isopropenylcyclohexan-1-ol (dihydrocarveol), 1-methyl-4-iso-propenylcyclohexan-3-ol, 4-isopropyl-1-methylcyclohexan-3-ol, 4-tert-butylcyclo-hexanol, 2-tert-butylcyclohexanol, 2-tert-butyl-4-methylcyclohexanol (rootanol), 4-isopropyl-cyclohexanol, 4-methyl-1-(1-methylethyl)-3-cyclohexen-1-ol, 2-(5,6,6-trimethyl-2-norbornyl)cyclohexanol, isobomylcyclohexanol, 3,3,5-trimethylcyclohexanol, 1-methyl-4-isopropylcyclohexan-3-ol, 1-methyl-4-isopropylcyclohexan-8-ol (dihydroterpineol), 1,2-dimethyl-3-(1-methylethyl) cyclohexan-1-ol, heptanol, 2,4-dimethylheptan-1-ol, 6-heptyl-5-hepten-2-ol (isolinalool), 2,4-dimethyl-2,6-heptandienol, 6,6-dimethyl-2-oxymethyl-bicyclo[3.1.1] hept-2-ene (myrtenol), 4-methyl-2,4-heptadien-1-ol, 3,4,5,6,6-pentamethyl-2-heptanol, 3,6-dimethyl-3-vinyl-5-hepten-2-ol, 6,6-dimethyl-3-hydroxy-2-methylenebicyclo

[3.1.1]heptane, 1,7,7-trimethylbicyclo[2.2.1]heptan-2-ol, 2,6-dimethylheptan-2-ol (dimetol), 2,6,6-trimethylbicyclo [1.3.3]heptan-2-ol, octanol, 2-octenol, 2-methyloctan-2-ol, 2-methyl-6-methylene-7-octen-2-ol (myrcenol), 7-methyloctan-1-ol, 3,7-dimethyl-6-octenol, 3,7-dimethyl-7-octenol, 3,7-dimethyl-6-octen-1-ol (citronellol), 3,7-dimethyl-2,6-octadien-1-ol (geraniol), 3,7-dimethyl-2,6-octadien-1-ol (nerol), 3,7-dimethyl-7-methoxyoctan-2-ol (osyrol), 3,7-dimethyl-1,6-octadien-3-ol (linalool), 3,7-dimethyloctan-1-ol (pelargol), 3,7-dimethyloctan-3-ol (tetrahydrolinalool), 2,4-octadien-1-ol, 3,7-dimethyl-6-octen-3-ol (dihydrolinalool), 2,6-dimethyl-7-octen-2-ol (dihydromyrcenol), 2,6-dimethyl-5,7-octadien-2-ol, 4,7-dimethyl-4-vinyl-6-octen-3-ol, 3-methyloctan-3-ol, 2,6-dimethyloctan-2-ol, 2,6-dimethyloctan-3-ol, 3,6-dimethyloctan-3-ol, 2,6-dimethyl-7-octen-2-ol, 2,6-dimethyl-3,5-octadien-2-ol (muguol), 3-methyl-1-octen-3-ol, 7-hydroxy-3,7-dimethyloctanal, 3-nonanol, 2,6-nonadien-1-ol, cis-6-nonen-1-ol, 6,8-dimethylnonan-2-ol, 3-(hydroxymethyl)-2-nonanone, 2-nonen-1-ol, 2,4-nonadien-1-ol, 3,7-dimethyl-1,6-nonadien-3-ol, decanol, 9-decenol, 2-benzyl-M-dioxa-5-ol, 2-decen-1-ol, 2,4-decadien-1-ol, 4-methyl-3-decen-5-ol, 3,7,9-trimethyl-1,6-decadien-3-ol (isobutyl linalool), undecanol, 2-undecen-1-ol, 10-undecen-1-ol, 2-dodecen-1-ol, 2,4-dodecadien-1-ol, 2,7,11-trimethyl-2,6,10-dodecatrien-1-ol (farnesol), 3,7,11-trimethyl-1,6,10,-dodecatrien-3-ol (nerolidol), 3,7,11,15-tetramethylhexadec-2-en-1-ol (phytol), 3,7,11,15-tetramethylhexadec-1-en-3-ol (iso phytol), benzyl alcohol, p-methoxy benzyl alcohol (anisyl alcohol), para-cymen-7-ol (cuminyl alcohol), 4-methyl benzyl alcohol, 3,4-methylenedioxy benzyl alcohol, methyl salicylate, benzyl salicylate, cis-3-hexenyl salicylate, n-pentyl salicylate, 2-phenylethyl salicylate, n-hexyl salicylate, 2-methyl-5-isopropylphenol, 4-ethyl-2-methoxyphenol, 4-allyl-2-methoxyphenol (eugenol), 2-methoxy-4-(1-propenyl)phenol (isoeugenol), 4-allyl-2,6-dimethoxy-phenol, 4-tert-butylphenol, 2-ethoxy-4-methylphenol, 2-methyl-4-vinylphenol, 2-isopropyl-5-methylphenol (thymol), pentyl-ortho-hydroxy benzoate, ethyl 2-hydroxy-benzoate, methyl 2,4-dihydroxy-3,6-dimethylbenzoate, 3-hydroxy-5-methoxy-1-methylbenzene, 2-tert-butyl-4-methyl-1-hydroxybenzene, 1-ethoxy-2-hydroxy-4-propenylbenzene, 4-hydroxytoluene, 4-hydroxy-3-methoxybenzaldehyde, 2-ethoxy-4-hydroxybenzaldehyde, decahydro-2-naphthol, 2,5,5-trimethyl-octahydro-2-naphthol, 1,3,3-trimethyl-2-norbornanol (fenchol), 3a,4,5,6,7,7a-hexahydro-2,4-dimethyl-4,7-methano-1H-inden-5-ol, 3a,4,5,6,7,7a-hexahydro-3,4-dimethyl-4,7-methano-1H-inden-5-ol, 2-methyl-2-vinyl-5-(1-hydroxy-1-methylethyl) tetrahydrofuran, β-caryophyllene alcohol, vanillin, ethyl vanillin, and mixtures thereof.

More preferably, the fragrance raw material alcohol is selected from the group consisting of cis-3-hexen-1-ol, hawthanol [admixture of 2-(o-methylphenyl)ethanol, 2-(m-methylphenyl)ethanol, and 2-(p-methylphenyl)ethanol], heptan-1-ol, decan-1-ol, 2,4-dimethyl cyclohexane methanol, 4-methylbutan-1-ol, 2,4,6-trimethyl-3-cyclohexene-1-methanol, 4-(1-methylethyl)cyclohexane methanol, 3-(hydroxy-methyl)-2-nonanone, octan-1-ol, 3-phenylpropanol, Rhodinol 70 [3,7-dimethyl-7-octenol, 3,7-dimethyl-6-octenol admixture], 9-decen-1-ol, α-3,3-trimethyl-2-norborane methanol, 3-cyclohexylpropan-1-ol, 4-methyl-1-phenyl-2-pentanol, 3,6-dimethyl-3-vinyl-5-hepten-2-ol, phenyl ethyl methanol; propyl benzyl methanol, 1-methyl-4-isopropenylcyclohexan-3-ol, 4-isopropyl-1-methylcyclohexan-3-ol (menthol), 4-tert-butylcyclohexanol, 2-tert-butyl-4-methylcyclohexanol, 4-isopropylcyclo-hexanol, trans-decahydro-β-naphthol, 2-tert-butylcyclohexanol, 3-phenyl-2-propen-1-ol, 2,7,11-trimethyl-2,6,10-dodecatrien-1-ol, 3,7-dimethyl-2,6-octadien-1-ol (geraniol), 3,7-dimethyl-2,6-octadien-1-ol (nerol), 4-methoxybenzyl alcohol, benzyl alcohol, 4-allyl-2-methoxyphenol, 2-methoxy-4-(1-propenyl)phenol, vanillin, and mixtures thereof.

Step (c) of the present process can be conducted in the presence of a suitable solvent or an excess amount of the fragrance raw material alcohol may be used as a solvent. Non-limiting examples of suitable solvents include dichloromethane, 1,2-dichloroethane, 1,2,3-trichloroethane, pentane, hexane, tetrahydrofuran, diethyl ether, benzene, toluene, xylene, 1,4-dioxane, acetonitrile, N,N-dimethylformamide (DMF), dimethylsulfoxide (DMSO), hexamethyl phosphoramide (HMPA), and mixtures thereof.

The reaction of Step (c) may be successfully conducted, depending upon the reactivity of the reagents, the scope of the reaction, and other mitigating parameters, at a temperature of from about 0° C., preferably from about 22° C. (approximately room temperature), more preferably from about 40° C., to about 200° C., preferably to about 150° C., more preferably to about 100° C., most preferably to about 80° C.

Included in Step (c) of the present invention is a provision for neutralizing any base present from Step (a) above. In a preferred embodiment of the present process, Step (c) is conducted under an inert atmosphere. In addition, an amount of a suitable acid catalyst may be added to the reaction of Step (c).

The product thus obtained from Step (c) of the present process can be purified by any conventional means depending upon the form physical form of the obtained β-ketoester. Non-limiting examples include chromatography, crystalizedion, distillation, sublimation, etc.

The following non-limiting example illustrates the present process.

Preparation of 3,7-Dimethyl-1,6-octadien-3-yl 3-(β-naphthyl)-3-oxo-propionate (linalyl (2-naphthoyl) acetoacetate)

Sodium hydride (1.26 g, 0.057 mol, 95%) is charged to a 250 mL three-necked round-bottomed flask fitted with a magnetic stirrer, ice bath, addition funnel, internal thermometer and argon inlet. The contents of the reaction vessel are slurried with 50 mL of tetrahydrofuran (THF) and subsequently cooled to 0° C. 2,2-dimethyl-1,3-dioxan-4,6-dione (Meldrum's acid) (3.78 g, 0.026 mol) is dissolved in 20 mL of THF and the solution is subsequently added over 15 min. The evolution of gas indicates the reaction is ensuing. After 30 min, 2-naphthoyl chloride (5.00 g, 0.026 mol) which is dissolved in 30 mL of THF is added over 15 min. The mixture is allowed to warm to room temperature and stirred for 72 h. A solution of 3,7-dimethyl-1,6-octadien-3-ol (linalool) (4.05 g, 0.026 mol) dissolved in 30 mL of THF is added over 30 min. The mixture is heated to reflux for 18 h. The cooled mixture is poured into 100 mL of water and extracted with ether (50 mL) three times. The organic layers are washed with saturated $NaHCO_3$ solution, water, dried over $MgSO_4$, filtered, concentrated by rotary evaporation and purified by flash chromatography to yield 3,7-dimethyl-1,6-octadien-3-yl 3-(β-naphthyl)-3-oxo-propionate.

What is claimed is:

1. A process for preparing a β-ketoester fragrance pro-accord comprising the steps of:
   a) reacting in the presence of a base a 1,3-dioxane-4,6-dione having the formula:

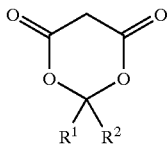

wherein $R^1$ and $R^2$ are each independently $C_1$–$C_{10}$ alkyl, $C_2$–$C_{10}$ alkenyl, $C_7$–$C_{22}$ alkylenearyl, $C_6$–$C_{10}$ aryl, and mixtures thereof; with an activated acyl group having the formula:

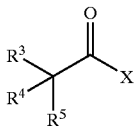

wherein $R^3$, $R^4$, and $R^5$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_1$–$C_{30}$ substituted or unsubstituted linear alkoxy, $C_3$–$C_{30}$ substituted or unsubstituted branched alkoxy, $C_3$–$C_{30}$ substituted or unsubstituted cyclic alkoxy, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl; or $R^3$, $R^4$, and $R^5$ can be taken together to form $C_6$–$C_{30}$ substituted or unsubstituted aryl; and mixtures thereof; X is an acyl activating unit; to form an acyl 1,3-dioxane-4,6-dione, the enol tautomer of which having the formula:

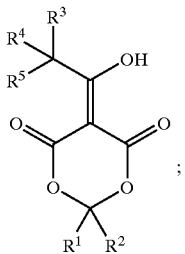

b) optionally, isolating said acyl 1,3-dioxane-4,6-dione; and
c) reacting said acyl 1,3-dioxane-4,6-dione from step (a) or (b) with a fragrance raw material alcohol having the formula:

ROH wherein R is selected from the group consisting of $C_8$ or higher alkyl, alkenyl, alkynyl, aryl, alkylaryl, alkylheteroaryl and heteroaryl moieties; said moieties being linear or branched, and substituted or unsubstituted; to form a β-ketoester pro-accord having the formula:

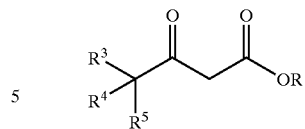

wherein $R^3$, $R^4$, and $R^5$ are as defined herein above.

2. A process according to claim 1 wherein step (a) is performed in the presence of a solvent.

3. A process according to claim 2 wherein said solvent is selected from the group consisting of dichloromethane, 1,2-di chloroethane, 1,2,3-trichloroethane, pentane, hexane, tetrahydrofuran, diethyl ether, benzene, toluene, xylene, 1,4-dioxane, acetonitrile, N,N-dimethylformamide, dimethyl sulfoxide, hexamethyl phosphoramide and mixtures thereof.

4. A process according to claim 3 wherein said solvent is dichloromethane or tetrahydrofuran.

5. A process according to claim 1 wherein step (a) is performed at a temperature of form about –70° C. to about 100° C.

6. A process according to claim 1 wherein said base is selected from the group consisting of alkylamines, aromatic amines, polymeric amines, organo lithium compounds, alkali metal hydroxides, alkaline earth metal hydroxides, alkali metal carbonates, alkaline earth metal carbonate, alkali metal hydrides, alkaline earth metal hydrides, and mixtures thereof.

7. A process according to claim 6 wherein said base is pyridine or sodium hydride.

8. A process according to claim 1 wherein $R^1$ and $R^2$ are each methyl.

9. A process according to claim 1 wherein X is chlorine.

10. A process according to claim 1 wherein $R^3$, $R^4$, and $R^5$ are taken together to form a naphthyl moiety.

11. A process according to claim 1 wherein said fragrance raw material alcohol ROH is selected from the group consisting of linalool, dihydromyrcenol, menthol, and mixtures thereof.

12. A process according to claim 1 wherein step (c) is performed at a temperature of from 30° C. to about 100° C.

13. A process according to claim 1 wherein step (c) is performed in the presence of a solvent.

14. A process according to claim 13 wherein said solvent is selected from the group consisting of dichloromethane, 1,2-dichloroethane, 1,2,3-trichloroethane, pentane, hexane, tetrahydrofuran, diethyl ether, benzene, toluene, xylene, 1,4-dioxane, acetonitrile, N,N-dimethylformamide, dimethyl sulfoxide, hexamethyl phosphoramide and mixtures thereof.

15. A process according to claim 1 wherein step (c) further comprises an acid catalyst.

16. A process according to claim 1 wherein the fragrance raw material alcohol ROH in step (c) has a molecular weight greater than or equal to 100 g/mol.

17. A process according to claim 1 wherein the fragrance raw material alcohol of step (c) is a mixture of one or more fragrance raw material alcohols.

18. A process for preparing a βketoester fragrance pro-accord comprising the steps of:
a) reacting in the presence of a base 2,2-dimethyl-1,3dioxane-4,6-dione having the formula:

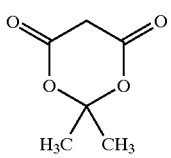

with an acyl halide having the formula:

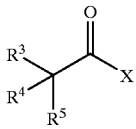

$R^3$, $R^4$ and $R^5$ are each independently hydrogen, $C_1$–$C_{16}$ substituted or unsubstituted linear alkyl, $C_3$–$C_{16}$ substituted or unsubstituted branched alkyl, or $R^3$; $R^4$, and $R^5$ are taken together to form $C_6$–$C_{30}$ substituted or unsubstituted phenyl, naphthyl, and mixtures thereof; X is selected from the group consisting of chlorine, bromine, iodine, and mixtures thereof; to form an acyl 2,2-dimethly-1,3-dioxane-4,6-dione, the enol tautomer of which having the formula:

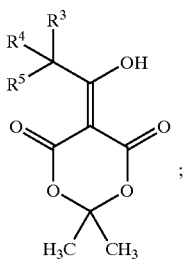

b) optionally, isolating said acyl 2,2-dimethyl-1,3-dioxane-4,6-dione; and c) reacting said acyl 2,2-dimethly-1,3-dioxane-4,6-dione from step (a) or (b) with a fragrance raw material alcohol having the formula:

ROH wherein R is selected from the group consisting of 3,7-dimethyl-1,6octadien-3-yl, 2,6-dimethyl-7-octen-2-yl, (a,a-4-trimethyl-3-cyclohexeneyl)methyl, cis 3-hexen-1yl, 9-decen-1-yl, 2,6-dimethyl-3,5-octadien-2-yl, 3,7-dimethyl-6-octen-1-yl, 3,7-dimethyl-2,6-octadien-1yl, and mixtures thereof; to form a b-ketoester fragrance pro-accord having the formula:

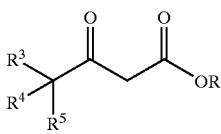

wherein R is selected from the group consisting of 3,7-dimethyl-1,6-octadien-3-yl, 2,6-dimethyl-7-octen-2-yl, (a,a-4-trimethyl-3-cyclohexenyl)methyl, cis 3-hexen-1-yl, 9-decen-1-yl, 2,6-dimethyl-3,5-octadien-2-yl, 3,7-dimethyl-6-octen-1-yl, 3,7-dimethyl-2,6-octadien-1-yl, and mixtures thereof; $R^3$, $R^4$, and $R^5$ are the same as defined herein above.

19. A process for preparing 3,7-dimethyl-1,6-octadien-3-yl 3-(b-naphthyl)-3-oxo-propionate comprising the steps of:

a) reacting in the presence of a base 2,2-dimethyl-1,3-dioxane-4,6-dione having the formula:

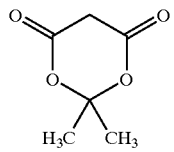

with b-naphthoyl chloride to form 5-b-naphthoyl-2,2-dimethyl-1,3-dioxane-4,6-dione, the enol tautomer of which having the formula:

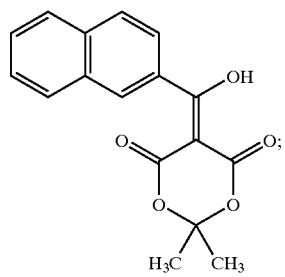

b) optionally, isolating said 5-b-naphthoyl-2,2-dimethyl-1,3-dioxane-4,6-dione; and c) reacting 5-b-naphthoyl-2,2-dimethyl-1,3-dioxane-4,6-dione from step (a) or (b) with linalool to form 3,7-dimethyl-1,6-octadien-3-yl 3-(b-naphthyl)-3-oxo-propionate having the formula:

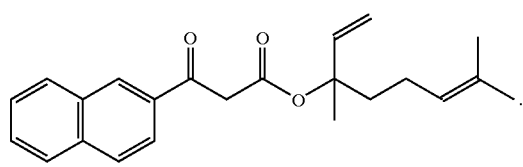

20. A process according to claim 18 wherein the fragrance raw material alcohol of step (c) is a mixture of linalool and one or more other fragrance raw material alcohols.

21. A process for preparing a β-ketoester fragrance pro-accord comprising the steps of:

a) reacting in the presence of a base a 1,3-dioxane-4,6-dione having the formula:

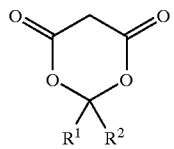

wherein $R^1$ and $R^2$ are each independently $C_1$–$C_{10}$ alkyl, $C_2$–$C_{10}$ alkenyl, $C_7$–$C_{22}$ alkylenearyl, $C_6$–$C_{10}$ aryl, and mixtures thereof; with an activated acyl group having the formula:

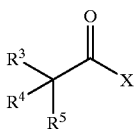

wherein $R^3$, $R^4$, and $R^5$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_1$–$C_{30}$ substituted or unsubstituted linear alkoxy, $C_3$–$C_{30}$ substituted or unsubstituted branched alkoxy, $C_3$–$C_{30}$ substituted or unsubstituted cyclic alkoxy, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl; or $R^3$, $R^4$, and $R^5$ can be taken together to form $C_6$–$C_{30}$ substituted or unsubstituted aryl; and mixtures thereof; X is an acyl activating unit; to form an acyl 1,3-dioxane-4,6-dione, the enol tautomer of which having the formula:

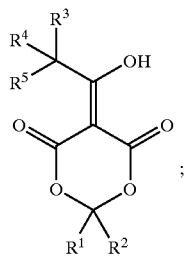

b) optionally, isolating said acyl 1,3-dioxane-4,6-dione; and c) reacting said acyl 1,3-dioxane-4,6-dione from step (a) or (b) with a fragrance raw material alcohol selected from the group consisting of 2,4-dimethyl-3-cyclohexene-1-methanol (Floralol), 2,4-dimethyl cyclohexane methanol (Dihydro floralol), 5,6-dimethyl-1-methylethenylbicyclo[2.2.1]hept-5-ene-2-methanol (Arbozol), α,α,4-trimethyl-3-cyclohexen-1-methanol (α-terpineol), 2,4,6-trimethyl-3-cyclohexene-1-methanol (Isocyclo geraniol), 4-(1-methylethyl)cyclohexane methanol (Mayol), α-3,3-trimethyl-2-norborane methanol, 1,1-dimethyl-1-(4-methylcyclohex-3-enyl)methanol, 2-phenylethanol, 2-cyclohexyl ethanol, 2-(o-methylphenyl)-ethanol, 2-(m-methylphenyl)ethanol, 2-(p-methylphenyl) ethanol, 6,6-dimethylbicyclo-[3.1.1]hept-2-ene-2-ethanol (nopol), 2-(4-methylphenoxy)-ethanol, 3,3-dimethyl-Δ²-β-norbornane ethanol (patchomint), 2-methyl-2-cyclohexylethanol, 1-(4-isopropylcyclohexyl)-ethanol, 1-phenylethanol, 1,1-dimethyl-2-phenylethanol, 1,1-dimethyl-2-(4-methylphenyl)ethanol, 1-phenylpropanol, 3-phenylpropanol, 2-phenylpropanol (Hydrotropic Alcohol), 2-(cyclododecyl)propan-1-ol (Hydroxyambran), 2,2-dimethyl-3-(3-methylphenyl)-propan-1-ol (Majantol), 2-methyl-3-phenylpropanol, 3-phenyl-2-propen-1-ol (cinnamyl alcohol), 2-methyl-3-phenyl-2-propen-1-ol (methylcinnamyl alcohol), α-n-pentyl-3-phenyl-2-propen-1-ol (α-amyl-cinnamyl alcohol), ethyl-3-hydroxy-3-phenyl propionate, 2-(4-methylphenyl)-2-propanol, 3-(4-methylcyclohex-3-ene)butanol, 2-methyl-4-(2,2,3-trimethyl-3-cyclopenten-1-yl)butanol, 2-ethyl-4-(2,2,3-trimethylcyclopent-3-enyl)-2-buten-1-ol, 3-methyl-2-buten-1-ol (prenol), 2-methyl-4-(2,2,3-trimethyl-3-cyclopenten-1-yl)-2-buten-1-ol, ethyl 3-hydroxybutyrate, 4-phenyl-3-buten-2-ol, 2-methyl-4-phenylbutan-2-ol, 4-(4-hydroxyphenyl)butan-2-one, 4-(4-hydroxy-3-methoxyphenyl)-butan-2-one, 3-methyl-pentanol, 3-methyl-3-penten-1-ol, 1-(2-propenyl)cyclopentan-1-ol (plinol), 2-methyl-4-phenylpentanol (Pamplefleur), 3-methyl-5-phenylpentanol (Phenoxanol), 2-methyl-5-phenylpentanol, 2-methyl-5-(2,3-dimethyltricyclo[2.2.1.0$^{(2,6)}$]hept-3-yl)-2-penten-1-ol (santalol), 4-methyl-1-phenyl-2-pentanol, 5-(2,2,3-trimethyl-3-cyclopentenyl)-3-methylpentan-2-ol (sandalore), (1-methyl-bicyclo[2.1.1]hepten-2-yl)-2-methylpent-1-en-3-ol, 3-methyl-1-phenylpentan-3-ol, 1,2-dimethyl-3-(1-methylethenyl)cyclopentan-1-ol, 2-isopropyl-5-methyl-2-hexenol, cis-3-hexen-1-ol, trans-2-hexen-1-ol, 2-isoproenyl-4-methyl-4-hexen-1-ol (Lavandulol), 2-ethyl-2-prenyl-3-hexenol, 1-hydroxymethyl-4-isopropenyl-1-cyclohexene (Dihydrocuminyl alcohol), 1-methyl-4-isopropenylcyclohex-6-en-2-ol (carvenol), 6-methyl-3-isopropenylcyclohexan-1-ol (dihydrocarveol), 1-methyl-4-iso-propenylcyclohexan-3-ol, 4-isopropyl-1-methylcyclohexan-3-ol, 4-tert-butylcyclo-hexanol, 2-tert-butylcyclohexanol, 2-tert-butyl-4-methylcyclohexanol (rootanol), 4-isopropyl-cyclohexanol, 4-methyl-1-(1-methylethyl)-3-cyclohexen-1-ol, 2-(5,6,6-trimethyl-2-norbornyl) cyclohexanol, isobornylcyclohexanol, 3,3,5-trimethylcyclohexanol, 1-methyl-4-isopropylcyclohexan-3-ol, 1-methyl-4-isopropylcyclohexan-8-ol (dihydroterpineol), 1,2-dimethyl-3-(1-methylethyl)cyclohexan-1-ol, heptanol, 2,4-dimethylheptan-1-ol, 6-heptyl-5-hepten-2-ol (isolinalool), 2,4-dimethyl-2,6-heptandienol, 6,6-dimethyl-2-oxymethyl-bicyclo[3.1.1]hept-2-ene (myrtenol), 4-methyl-2,4-heptadien-1-ol, 3,4,5,6,6-pentamethyl-2-heptanol, 3,6-dimethyl-3-vinyl-5-hepten-2-ol, 6,6-dimethyl-3-hydroxy-2-methylenebicyclo[3.1.1]heptane, 1,7,7-trimethylbicyclo[2.2.1]heptan-2-ol, 2,6-dimethylheptan-2-ol (dimetol), 2,6,6-trimethylbicyclo[1.3.3]heptan-2-ol, octanol, 2-octenol, 2-methyloctan-2-ol, 2-methyl-6-methylene-7-octen-2-ol (myrcenol), 7-methyloctan-1-ol, 3,7-dimethyl-6-octenol, 3,7-dimethyl-7-octenol, 3,7-dimethyl-6-octen-1-ol (citronellol), trans-3,7-dimethyl-2,6-octadien-1-ol (geraniol), cis-3,7-dimethyl-2,6-octadien-1-ol (nerol), 3,7-dimethyl-7-methoxyoctan-2-ol (osyrol), 3,7-dimethyl-1,6-octadien-3-ol (linalool), 3,7-dimethyloctan-1-ol (pelargol), 3,7-dimethyloctan-3-ol (tetrahydrolinalool), 2,4-octadien-1-ol, 3,7-dimethyl-6-octen-3-ol (dihydrolinalool), 2,6-dimethyl-7-octen-2-ol (dihydromyrcenol), 2,6-dimethyl-5,7-octadien-2-ol, 4,7-dimethyl-4-vinyl-6-octen-3-ol, 3-methyloctan-3-ol, 2,6-dimethyloctan-2-ol, 2,6-dimethyloctan-3-ol, 3,6-dimethyloctan-3-ol, 2,6-dimethyl-7-octen-2-ol, 2,6-dimethyl-3,5-octadien-2-ol (muguol), 3-methyl-1-octen-3-ol, 7-hydroxy-3,7-dimethyloctanal, 3-nonanol, 2,6-nonadien-1-ol, cis-6-nonen-1-ol, 6,8-dimethylnonan-2-ol, 3-(hydroxymethyl)-2-nonanone, 2-nonen-1-ol, 2,4-nonadien-1-ol, 3,7-dimethyl-1,6- nonadien-3-ol, decanol, 9-decenol, 2-benzyl-M-dioxa-5-ol, 2-decen-1-ol, 2,4-decadien-1-ol, 4-methyl-3-decen-5-ol, 3,7,9-trimethyl-1,6-decadien-3-ol (isobutyl linalool), undecanol, 2-undecen-1-ol, 10-undecen-1-ol, 2-dodecen-1-ol, 2,4-dodecadien-1-ol, 2,7,11-trimethyl-2,6,10-dodecatrien-1-ol (farnesol), 3,7,11-trimethyl-1,6,10,-dodecatrien-3-ol (nerolidol), 3,7,11,15-tetramethylhexadec-2-en-1-ol (phytol), 3,7,11,15-tetramethylhexadec-1-en-3-ol (iso phytol), pentanol, p-methoxy benzyl alcohol (anisyl alcohol), paracymen-7-ol (cuminyl alcohol), 4-methyl benzyl alcohol, 3,4-methylenedioxy benzyl alcohol, methyl salicylate, benzyl salicylate, cis-3-hexenyl salicylate, n-pentyl salicylate, 2-phenylethyl salicylate, n-hexyl salicylate, 2-methyl-5-isopropylphenol, 4-ethyl-2-methoxyphenol, 4-allyl-2-methoxyphenol (eugenol), 2-methoxy-4-(1-propenyl)phenol (isoeugenol), 4-allyl-2,6-dimethoxy-phenol, 4-tert-butylphenol, 2-ethoxy-4-methylphenol, 2-methyl-4-vinylphenol, 2-isopropyl-5-methylphenol (thymol), pentyl-ortho-hydroxy benzoate, ethyl 2-hydroxy-benzoate, methyl 2,4-dihydroxy-3,6-dimethylbenzoate, 3-hydroxy-5-methoxy-1-methylbenzene, 2-tert-butyl-4-methyl-1-hydroxybenzene, 1-ethoxy-2-hydroxy-4-propenylbenzene, 4-hydroxytoluene, 4-hydroxy-3-methoxybenzaldehyde, 2-ethoxy-4-hydroxybenzaldehyde, decahydro-2-naphthol, 2,5,5-trimethyl-octahydro-2-naphthol, 1,3,3-trimethyl-2-norbornanol (fenchol), 3a,4,5,6,7,7a-hexahydro-2,4-dimethyl-4,7-methano-1H-inden-5-ol, 3a,4,5,6,7,7a-hexahydro-3,4-dimethyl-4,7-methano-1H-inden-5-ol, 2-methyl-2-vinyl-5-(1-hydroxy-1-methylethyl)tetra hydrofuran, 3-cyclohexylpropan-1-ol, propyl benzyl methanol, β-caryophyllene alcohol, vanillin, ethyl vanillin, and mixtures thereof; to form a β-ketoester fragrance pro-accord having the formula:

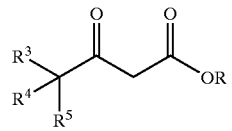

wherein $R^3$, $R^4$, and $R^5$ are the same as defined herein above.

* * * * *